United States Patent
Christy et al.

(10) Patent No.: US 9,285,501 B2
(45) Date of Patent: Mar. 15, 2016

(54) MULTIPLE SENSOR SYSTEM AND METHOD FOR MAPPING SOIL IN THREE DIMENSIONS

(75) Inventors: Colin Christy, Salina, KS (US); Paul Drummond, Salina, KS (US); Giyoung Kweon, Salina, KS (US); Chase Maxton, Salina, KS (US); Kenton Dreiling, Salina, KS (US); Kyle Jensen, Salina, KS (US); Eric Lund, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 1517 days.

(21) Appl. No.: 12/612,375

(22) Filed: Nov. 4, 2009

(65) Prior Publication Data

US 2011/0106451 A1    May 5, 2011

Related U.S. Application Data

(60) Provisional application No. 61/111,334, filed on Nov. 4, 2008.

(51) Int. Cl.
*G01N 31/00* (2006.01)
*G01N 33/24* (2006.01)
*G01V 11/00* (2006.01)
*G01N 21/359* (2014.01)
*G01N 21/85* (2006.01)
*G01N 21/3563* (2014.01)

(52) U.S. Cl.
CPC .............. *G01V 11/00* (2013.01); *G01N 21/359* (2013.01); *G01N 21/3563* (2013.01); *G01N 21/8507* (2013.01)

(58) Field of Classification Search
CPC .... G01V 11/00; G01V 11/002; G01N 21/359; G01N 21/8507; G01N 21/3563; G01N 1/2294; G01N 1/2205; G01N 1/4005
USPC ............... 702/5, 28; 73/863, 863.01, 864.45, 73/864.91; 356/303, 326; 250/253; 324/347
See application file for complete search history.

(56) References Cited

U.S. PATENT DOCUMENTS 5,038,040 A * 8/1991 Funk ................... G01N 21/3563
                                                    250/339.02
5,461,229 A * 10/1995 Sauter .................... G01N 21/71
                                                    250/253

(Continued)

*Primary Examiner* — Toan Le
*Assistant Examiner* — Jeffrey Aiello
(74) *Attorney, Agent, or Firm* — Jeffrey L. Thompson; Thompson & Thompson, PA

(57) ABSTRACT

A multi-sensor system rapidly measures diffuse reflectance of soil, soil conductivity, and other soil properties in situ, in three dimensions. The system includes a tractor-drawn implement containing a sensor shank used for X-Y axis measurements, a hydraulic probe implement containing a sensor probe for –Z axis measurements, and a set of visible and near-infrared spectrometers, controls, and firmware that are shared by each implement. Both implements include optical sensors and soil electrical conductivity sensors. The probe implement incorporates a sensor that measures insertion force, and the shank implement includes a soil temperature sensor. These combinations of sensors are used to calibrate the system and to characterize the soil properties within a field or area. Geo-referenced soil measurements are collected with the shank implement to identify optimal locations for conducting sensor probe insertions. The probe implement is then used for sensor probing and for collecting soil core samples for lab analysis.

8 Claims, 12 Drawing Sheets

(56) References Cited

U.S. PATENT DOCUMENTS

| | | | | |
|---|---|---|---|---|
| 5,524,560 A * | 6/1996 | Carter | | 111/200 |
| 5,604,582 A * | 2/1997 | Rhoads | | G01J 3/2823 250/458.1 |
| 5,721,679 A * | 2/1998 | Monson | | 701/50 |
| 5,739,536 A * | 4/1998 | Bucholtz | | G01J 3/02 250/253 |
| 5,828,452 A * | 10/1998 | Gillispie et al. | | 356/328 |
| 5,841,282 A * | 11/1998 | Christy | | A01B 79/005 111/118 |
| 6,356,830 B1 * | 3/2002 | Adamchuck | | A01B 79/005 111/118 |
| 6,864,826 B1 * | 3/2005 | Stove | | G01N 22/00 342/134 |
| 2002/0026824 A1 * | 3/2002 | Frost | | B60Q 9/006 73/84 |
| 2003/0216894 A1 * | 11/2003 | Ghaboussi | | E02D 1/022 703/2 |
| 2004/0118199 A1 * | 6/2004 | Frost | | E02D 1/022 73/152.51 |
| 2007/0013908 A1 * | 1/2007 | Lee | | G01J 3/02 356/301 |
| 2007/0112258 A1 * | 5/2007 | Soyemi | | A61B 5/0059 600/310 |
| 2011/0106451 A1 * | 5/2011 | Christy | | G01N 21/359 702/5 |
| 2014/0358381 A1 * | 12/2014 | Holland | | G01N 21/55 701/50 |

\* cited by examiner

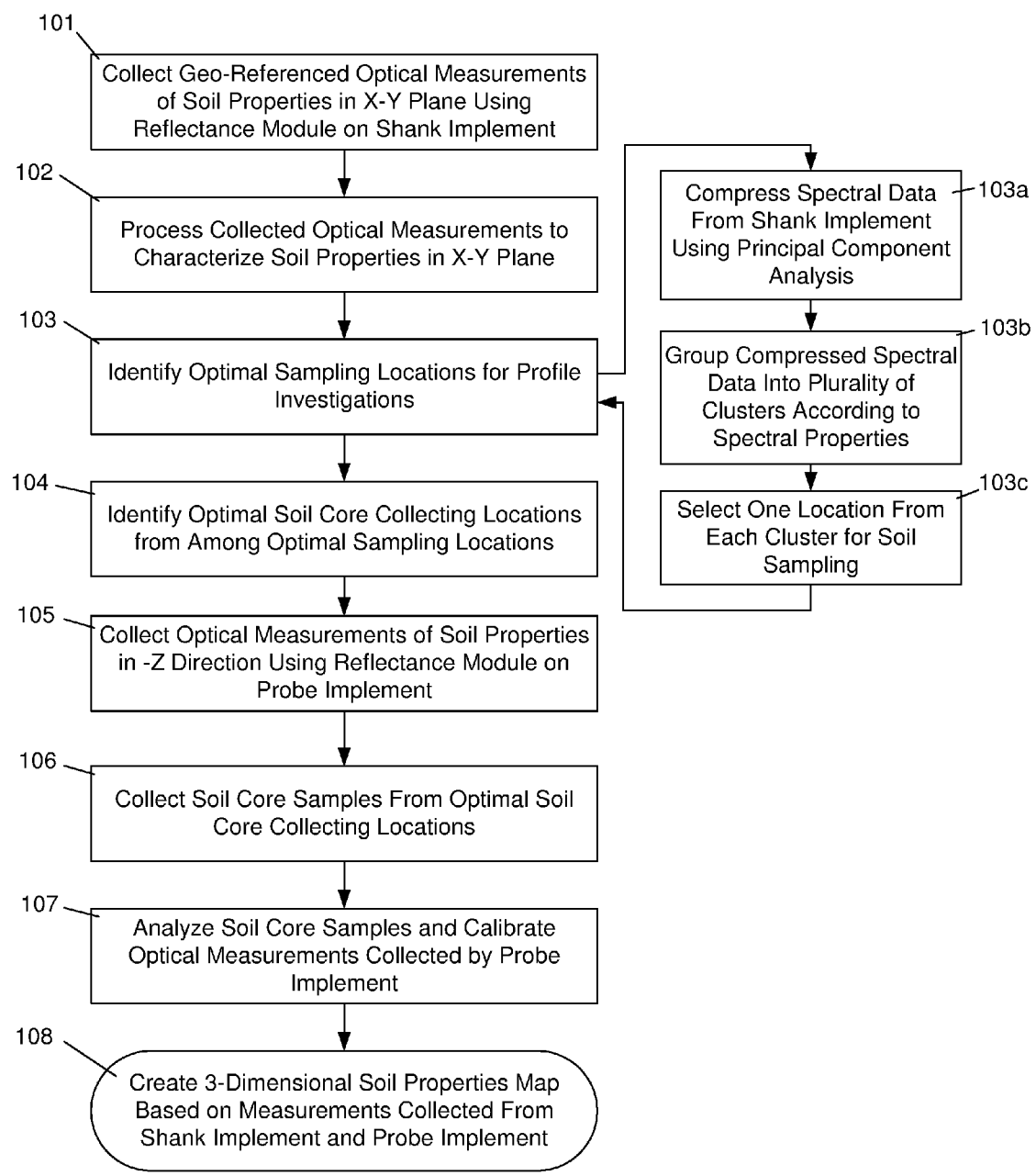

MULTIPLE SENSOR SYSTEM AND METHOD FOR MAPPING SOIL IN THREE DIMENSIONS

RELATED APPLICATIONS

This application claims priority of U.S. Provisional Application No. 61/111,334 filed on Nov. 4, 2008. This application is also related to the subject matter of U.S. patent application Ser. No. 12/253,594 filed on Oct. 17, 2008, which claims priority of U.S. Provisional Application No. 60/982,395 filed on Oct. 24, 2007. The entire contents of these prior applications are incorporated herein by reference.

BACKGROUND OF THE INVENTION

1. Field of the Invention

The present invention relates generally to methods and devices for analyzing and mapping soil properties within a field. In particular, the present invention relates to methods and devices for mapping soils within a field in three dimensions using multiple sensors.

2. Description of the Related Art

Mapping soil properties precisely, especially identifying differences hidden within the soil profile, has proven challenging for soil scientists and soil classifiers. While GPS technology provides precise positional information, quantitative information about the soil properties that exist within the profile at each location remains a limiting factor. The number of soil samples needed to accurately map soil variability is impractical using conventional sampling and analysis methods.

One of the important issues involving in situ soil measurements relates to reducing atmospheric carbon by increasing the amount of carbon stored in the soil. For carbon-trading to include agricultural soil sequestration, accurate baseline estimates of soil carbon, coupled with equally precise follow-up measurements, must be achievable. Two aspects of soil carbon makes this especially challenging: 1) expected carbon increases are small relative to the amount of carbon variability within the field, and 2) changes in soil bulk density must also be measured. Both of these measurements are traditionally accomplished in a laboratory, which requires extracting soil from the field, transporting to the lab, drying, and measurement. The cost for each sample result precludes intense sampling and analysis.

Rapid investigation using soil sensors can address this problem, provided the sensing technology relates to the soil properties of interest. Soil measurements using diffuse near-infrared spectroscopy (NIR) have been shown to relate closely to soil carbon levels. Reflectance in the visible (VIS) and in the NIR portion of the electromagnetic spectrum are highly influenced by molecules containing strong bonds between relatively light atoms. These bonds tend to absorb energy at overtones and combinations of the mid infrared fundamental vibration frequencies. The predominant absorbers in this region are the C—H, N—H, and O—H functional groups, making the VIS-NIR region ideal for quantifying forms of carbon, nitrogen and water respectively. Soil electrical conductivity (EC) has been shown to relate to soil texture and soil moisture. Soil penetrometer probes measuring insertion force have been shown to relate to soil compactness. Since the factors affecting bulk density are soil moisture, texture, and compaction, using sensors to measure these factors individually holds significant potential for developing calibrations to soil bulk density.

Soil heterogeneity within a field and within the profile prevents simple characterization of soils. A device that maps the field in the X-Y direction, but at only one depth, would not identify changes in the profile. A device that probes into the profile, but at a limited and random number of sites, would likely not be able to capture all the variability within the field.

There is a need in the industry for a system that characterizes the X-Y variability of soils in a field, identifies areas that require profile investigations, and characterizes the −Z variability at those sites.

SUMMARY OF THE INVENTION

The present invention provides a multi-sensor system capable of rapidly measuring diffuse reflectance of soil, soil conductivity, and other soil properties in situ, in three dimensions. The system includes a tractor-drawn implement containing a sensor shank used for X-Y axis measurements, a hydraulic probe implement containing a sensor probe for −Z axis measurements, and a set of visible and near-infrared spectrometers, controls, and firmware that are shared by each implement. In addition to the optical sensors, both implements include soil electrical conductivity sensors. The probe implement incorporates a sensor that measures insertion force, and the shank implement includes a soil temperature sensor. These combinations of sensors are used to calibrate the system to soil constituents and to characterize the soil properties within a field or area. In use, the shank implement is first used to collect geo-referenced soil measurements to map the soil properties in a generally horizontal X-Y plane. The measurement data collected by the shank implement is then reviewed by firmware in the operating system to identify optimal locations in the field for conducting sensor probe insertions using the probe implement. The probe implement is then used for sensor probing. Following sensor probing, a soil coring probe is installed on the probe implement for collecting soil core samples for lab analysis. From these analyses, calibrations to specific soil properties are made.

According to one aspect of the present invention, a soil mapping system for mapping soils within a field in three dimensions is provided, comprising: a shank implement means for collecting spectroscopic measurements of soil in a field while traversing the field in a generally horizontal X-Y plane; a probe implement means having a sensor probe for collecting spectroscopic measurements of soil in a field while probing the field in a generally vertical −Z direction; and a common means for processing data collected by the shank implement means and the probe implement means to characterize soil properties of the field in three dimensions.

According to another aspect of the present invention, a method of mapping soil properties in a field in three dimensions, comprises: traversing a field with a reflectance module carried on a shank implement to collect optical measurements of soil properties in an X-Y plane at a first depth; processing said collected optical measurements to characterize the variability of the soil properties in the X-Y plane; identifying optimal sampling locations for profile investigations; and inserting a reflectance module carried on a probe implement vertically into the soil at said optimal sampling locations to collect optical measurements of soil properties in a −Z direction.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings:

FIG. 11 is a flowchart showing method steps for mapping soil properties in a field in three dimensions according to the present invention.

DETAILED DESCRIPTION OF THE INVENTION

Figure 1:
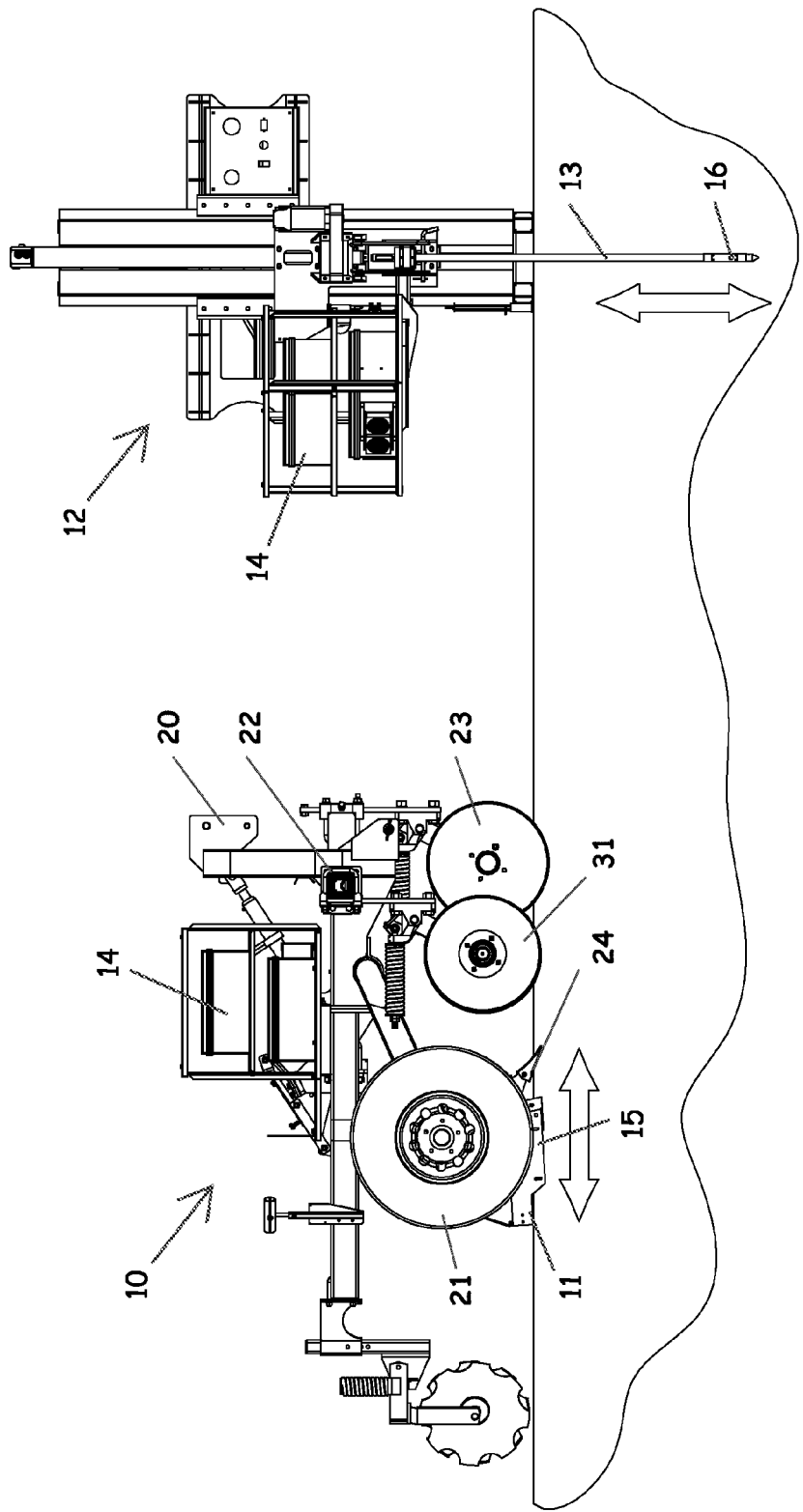
FIG. 1 is an elevation view showing a shank implement and a probe implement of a soil mapping system according to the present invention.
Figure 2:
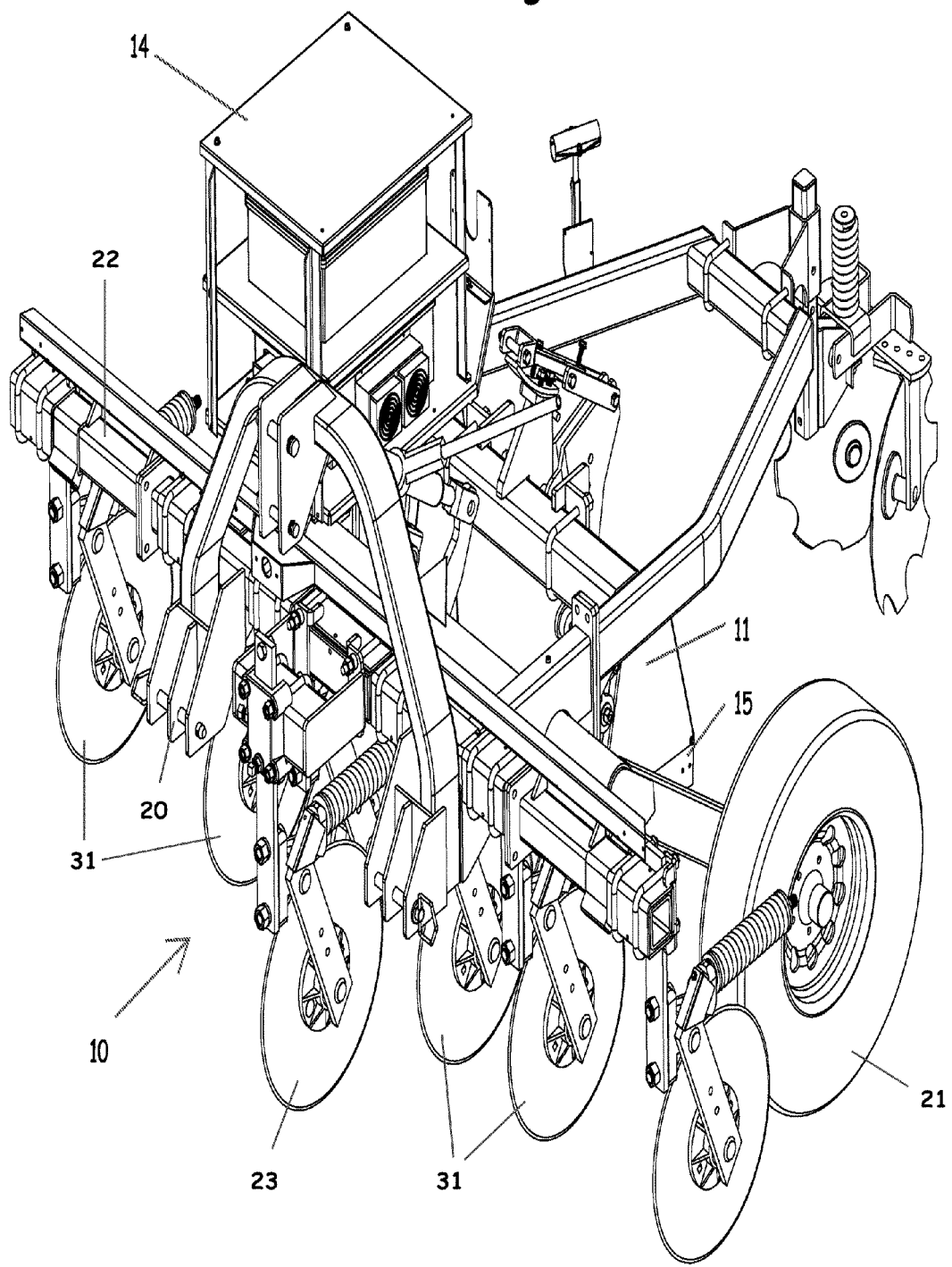
FIG. 2 is a perspective view of the shank implement of the soil mapping system shown in FIG. 1.
Figure 2A:
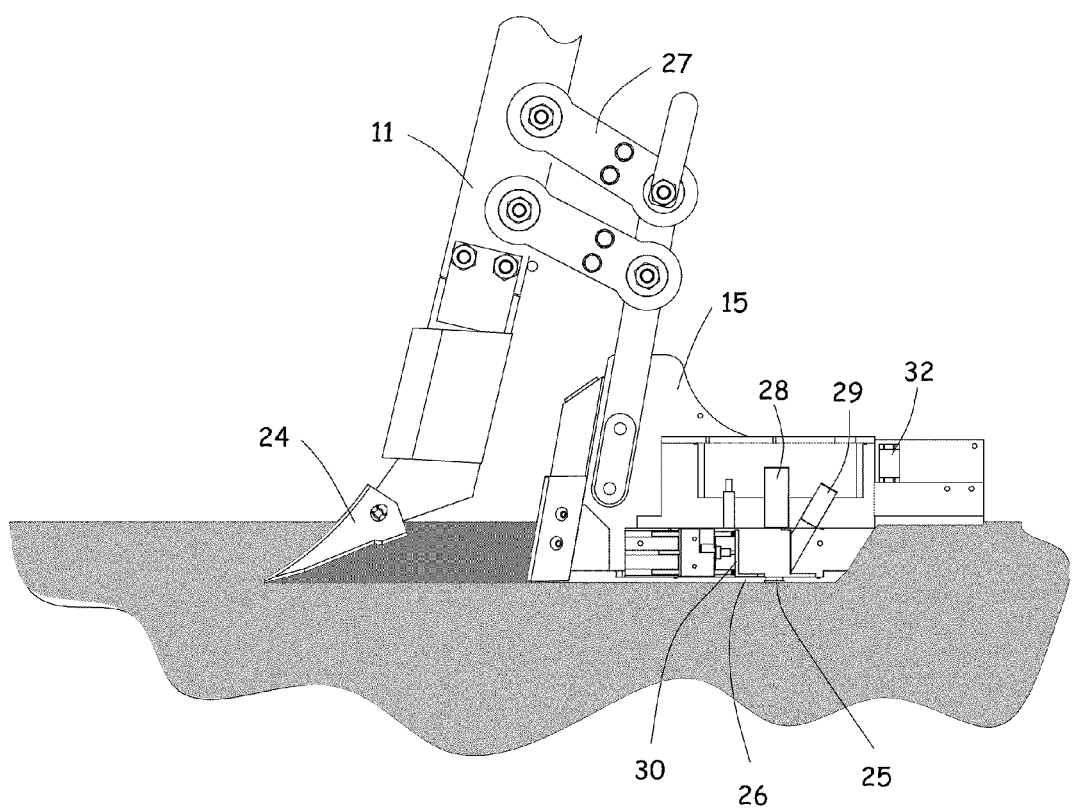
FIG. 2A is an elevation view of a shank assembly and reflectance module of the shank implement as they pass through soil during operation.
Figure 3:
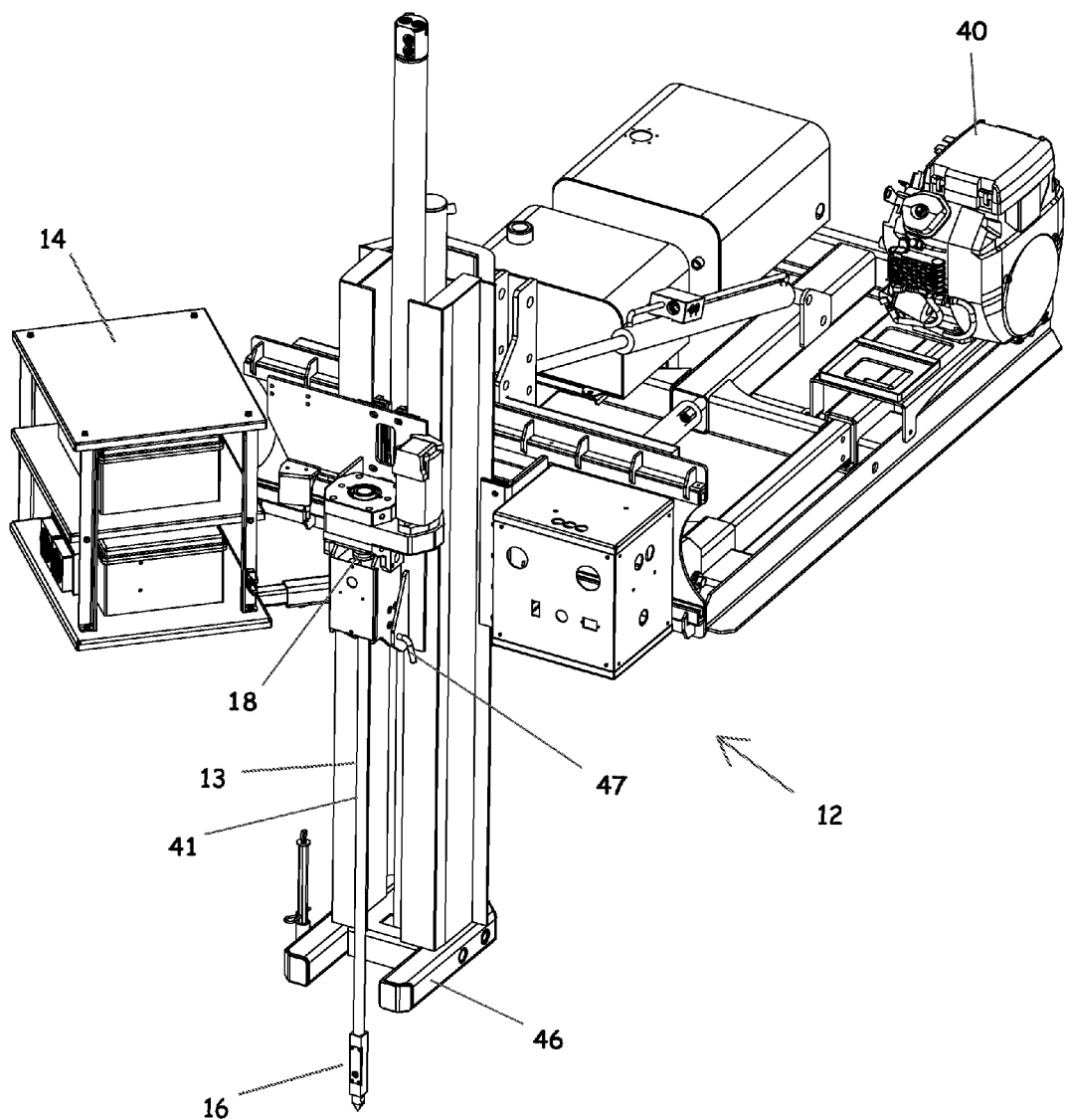
FIG. 3 is a perspective rear view of the probe implement of the soil mapping system shown in FIG. 1.

A mobile soil mapping system and method for mapping soils within a field in three dimensions using multiple sensors according to the present invention will now be described in detail with reference to FIGS. 1 to 11 of the accompanying drawings.

The soil mapping system of the present invention includes a tractor drawn implement 10 containing a sensor shank assembly 11 used for X-Y axis measurements, a hydraulic probe implement 12 containing a sensor probe 13 for –Z axis measurements, and a set of visible and near-infrared spectrometers 14, controls, and firmware that are shared by each implement 10, 12.

The shank implement 10 has a reflectance module 15 carried by the sensor shank assembly 11 to collect spectral data of the soil in a generally horizontal X-Y plane. The shank implement 10 also includes a shallow (e.g., 12 inch depth) soil electrical conductivity sensor 31, a deep (e.g., 30 inch depth) soil electrical conductivity sensor 32, and a soil temperature sensor 33. These components are used to collect additional soil data in the X-Y horizontal plane. Additional details of the shank implement 10 and the reflectance module 15 are described below.

The probe implement 12 has a reflectance module 16 carried at the lower end of the sensor probe 13 to collect spectral data of the soil in a generally vertical borehole (i.e., in the –Z direction). The probe implement 12 also includes a soil electrical conductivity sensor 17 at the lower tip of the sensor probe 13, and a sensor 18 that measures insertion force. Additional details of the probe implement 12 and the reflectance module 16 are described below.

Electronics

The two major soil-engaging components of the system (i.e., the shank reflectance module 15 and the probe reflectance module 16) share a common package of electronics including spectrometers, signal conditioning and processing hardware, auxiliary sensor controls, sensor monitors, and software. In one embodiment, the spectrometer package is a spectrophotometer controlled by a PC-based operating system. This package includes instrument control, data-recording, and data standardization functions. For example, the spectrometers can collect measurements in the 350 to 2200 nm range at a rate of 20 spectra per second with an 8 nm resolution. To safeguard the equipment and the measurements, spectrometers are protected in a shock-mounted, climate-controlled, electronically-monitored case.

In order to insure that data collected with each system matches other systems from a common manufacturer, each unit undergoes a system transform at the factory. Each production spectrometer system is considered a slave instrument and calibrated from a master instrument, which is kept at the manufacturer. This master instrument is calibrated to known Avian reflectance standards. Keeping the master instrument calibrated to these standards allows the slave spectrometer units to be calibrated by a system traceable to these known standards. This allows the data collected from any instrument to be comparable, and compiled into libraries containing soil reflectance properties. This provides a method of leveraging local soil reflectance measurements made by the system.

A system check transform using four external references compensates for any instrument variation due to wear. At predetermined intervals during field use, typically every 20 minutes, the system requires collection of dark and reference measurements. The dark measurement completely eliminates the light source from the reflected light optic, and is used to compensate for imperfections in the spectrometer. In the reference measurement, a known reference material is placed in front of the optic. This is used to compensate for drift in the spectrometer and light source. On the shank implement, the dark and reference measurements are accomplished automatically with an internal shutter. On the probe implement, they are performed manually, by turning off the light source and by placing an external reference in front of the window.

While reflectance measurements are being recorded, auxiliary data and instrument data are simultaneously being recorded. An auxiliary instrument, which also controls the movements of the shank shutter during the dark—reference routine, collects the auxiliary data. The auxiliary data recorded while using the shank implement are electrical conductivity shallow (EC_SH), electrical conductivity deep (EC_DP), and soil temperature. The auxiliary data recorded while using the probe implement are electrical conductivity at the lower probe tip and insertion force. The system also records instrument data including the auxiliary case temperature, auxiliary case humidity, spectrometer case temperature, spectrometer case humidity, and control box temperature. The operating software monitors these and the user is alerted when any of these values are out of specification.

Shank Implement

The shank implement is designed to be pulled by a tractor or four wheel drive vehicle, traversing agricultural fields at speeds of 4 to 6 mph. Typically, fields are mapped on 50 to 60 foot transects, although data can be collected on any transect width chosen by the operator. Field conditions can range from un-tilled to completely tilled. All measurements are automatically geo-referenced with a GPS receiver.

The shank implement 10 has a hitch structure 20 for connecting to a towing vehicle, a set of support wheels 21, and a frame 22 on which the sensor shank assembly 11 and various other components are mounted. A fluted coulter 23 is connected to the implement 10 near the front of the frame 22. The coulter 23 functions to cut through crop residue and open a narrow slit in the soil. The shank assembly 11 contains a ripping tooth 24 that follows behind the coulter 23 and further opens the slit into a soil slot. The operating depth of the shank assembly 11 is adjustable relative to the frame 22 by using a series of adjustment holes or other adjustment mechanism.

The reflectance module 15 attaches directly behind the shank assembly 11 and is carried by the sensor shank assembly 11 to collect high quality spectral data of the soil in a generally horizontal X-Y plane. A sapphire window 25 is provided in a wear plate 26 on the bottom side of the reflectance module 15. The window 25 is arranged to maintain firm contact with the soil to prevent dust, mud, and ambient light from interfering with the spectral measurements. By not allowing any space between the window and the soil, there is no dust billowing up in front of the window, and any wet soil that might adhere to the window is cleaned off by the pressure of the window against the bottom of the soil slot. Finally, because the window is pressed flat against the slot, no ambient light can enter the view of the optical components. The reflectance module 15 mounts to the shank assembly 11 with a parallel linkage 27, which allows the reflectance module 15 to follow undulations in terrain and still maintain its proper orientation to the soil.

Inside the reflectance module is a first machined cavity containing a light source 28, such as a tungsten halogen bulb, and a second machined cavity containing an optical receiver lens 29. The light source 28 is used to illuminate the soil, and the optical receiver lens 29 is used to direct light reflected from the soil into a fiber optic for transmission to the spectrometer 14. The light source 28, receiver lens 29, and spectrometer 14 are used for collecting soil reflectance data.

An actuator moves a shutter 30 within the reflectance module 15 from an open position for collecting soil reflectance data, into two positions for collecting dark and reference measurements. The dark measurement position completely blocks the light source 28 from the receiver lens 29, and in the reference measurement position the actuator moves a known reference material in front of the receiver lens 29. Additional details of the reflectance module 15 of the shank implement 10 and its operation are described in the Applicants' U.S. Patent Application Publication No. 2009/0112475 A1.

In addition to the optical measurements provided by the spectrometer 14, the shank implement 10 collects measurements of soil electrical properties (EC). Soil EC is a measurement that integrates many soil properties including water content, soil texture, soil organic matter (OM), depth to claypans, cation exchange capacity (CEC), salinity, and exchangeable calcium (Ca) and magnesium (Mg). While some of these properties are detectable using the optical sensor of the reflectance module 15, including a sensor measurement from another technology family helps resolve the properties, and improves calibrations. Also, the EC depth of investigation is 30 inches, which provides soil profile information that is deeper than that investigated by the optical sensor contained in the reflectance module 15 of the shank implement 10.

The contact electrode method used on the shank implement injects electrical current into the soil through two insulated metal electrodes 31 that penetrate the soil surface, and measures the voltage drop between the two sources and two pairs of sensor electrodes. One pair measures soil EC at a 0 to 12 inch depth, and the second pair measures soil EC at a 0 to 30 inch depth. Additional details of the contact electrode method for measuring soil EC can be found in Applicants' prior U.S. Pat. No. 5,841,282.

A non-contact infrared soil temperature sensor 32 is located on a back side of the reflectance module 15. This measurement aids in calibration, as some soil properties' reflectance characteristics change with temperature. Since soil temperature in the near surface can be highly variable and affected by ground cover, aspect, slope, and other factors, measuring temperature improves soil property calibration results.

Probe Implement

The probe implement 12 is designed to hydraulically push a sensor probe 13 vertically into the soil profile in situ. The probe implement 12 can be configured with its own engine 40 and hydraulics, as shown in the embodiment illustrated in FIGS. 3 to 5 and 8, and mounted on a truck bed (not shown). Alternatively, the probe implement 12 can be attached to a tractor via a 3-point hitch 43, as shown in the embodiment illustrated in FIGS. 9 and 10.

The sensor probe 13 is constructed of a one-inch diameter, 40-inch long, hollow-stem probe rod 41. The sensor probe 13 has a replaceable conical tip 42 to aid in soil penetration. Embedded in the conical tip 42 is an EC contact pin 17, insulated from the probe rod 41. Electrical current is injected into the pin 17, and voltage drop is measured at the conical tip 42. Above the conical tip 42 is a replaceable reflectance module 16 threaded onto the probe rod 41. The reflectance module 16 is used by the probe implement 12 for collecting high quality spectral measurements.

On the side of the reflectance module 16 is a sapphire window 44, through which the soil is illuminated and the reflected light collected. This window 44 must maintain firm contact with the soil to prevent dust, mud, and ambient light from interfering with the spectral measurements. By not allowing any space between the window 44 and the soil, there is no dust billowing up in front of the window 44, and any wet soil that might adhere to the window 44 is cleaned off by the pressure of the window against the soil profile sidewall. Finally, because the window 44 is pressed firmly against the profile wall, no ambient light can enter the view of the optical components within the reflectance module 16.

Inside the probe reflectance module 16 are machined cavities holding a tungsten halogen bulb used to illuminate the soil, and an optical receiver lens 45 to direct reflected light into a fiber optic for transmission to the spectrometer 14. The arrangement of the tungsten halogen bulb and the optical receiver lens in the probe reflectance module 16 can be similar to the corresponding parts of the shank reflectance module 15.

At the top of the probe rod 41 is a load cell 18 that measures the insertion force required to insert the probe 13. The measured insertion force, reflectance and electrical conductivity of the soil profile can be used to determine moisture, texture and bulk density of the soil. An electronic string-pot records the depth during insertion of the probe 13 into the soil profile. The depth measurements and GPS location data are matched with the sensor values at each insertion.

At predetermined intervals, the operating software informs the operator of the need to collect a dark and reference measurement. On the probe implement 12, the operator initiates this sequence by pressing a button on the operating software screen, which shuts off the lamp to collect the dark measurement. Once the dark measurement is acquired, the operator places an external reference over the probe window 44, and the system collects the reference measurement.

Figure 4:
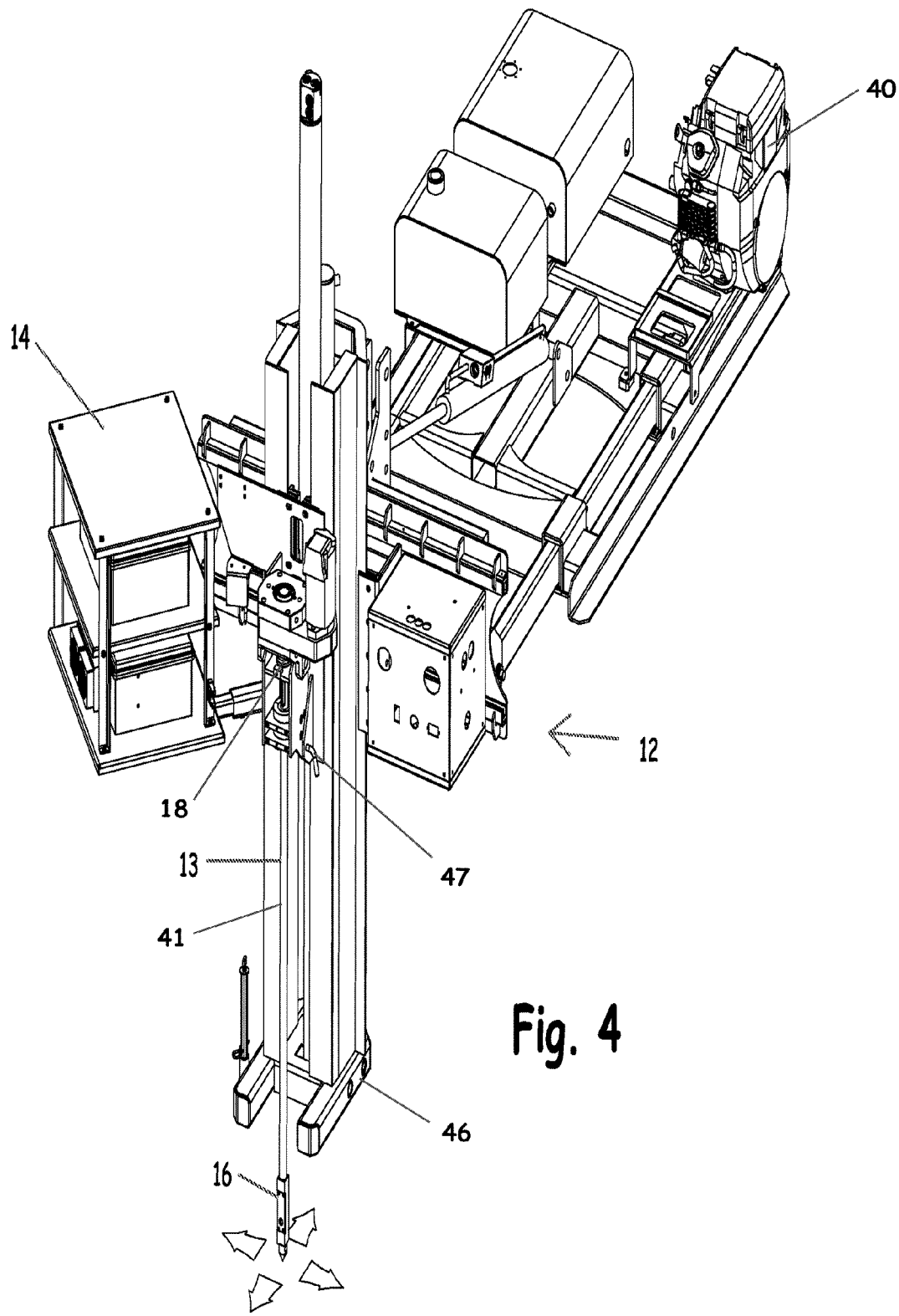
FIG. 4 is a perspective rear view of the probe implement of FIG. 3 showing the lateral and front-to-back shifting of the sensor probe to facilitate repeated insertions in close proximity.
Figure 5:
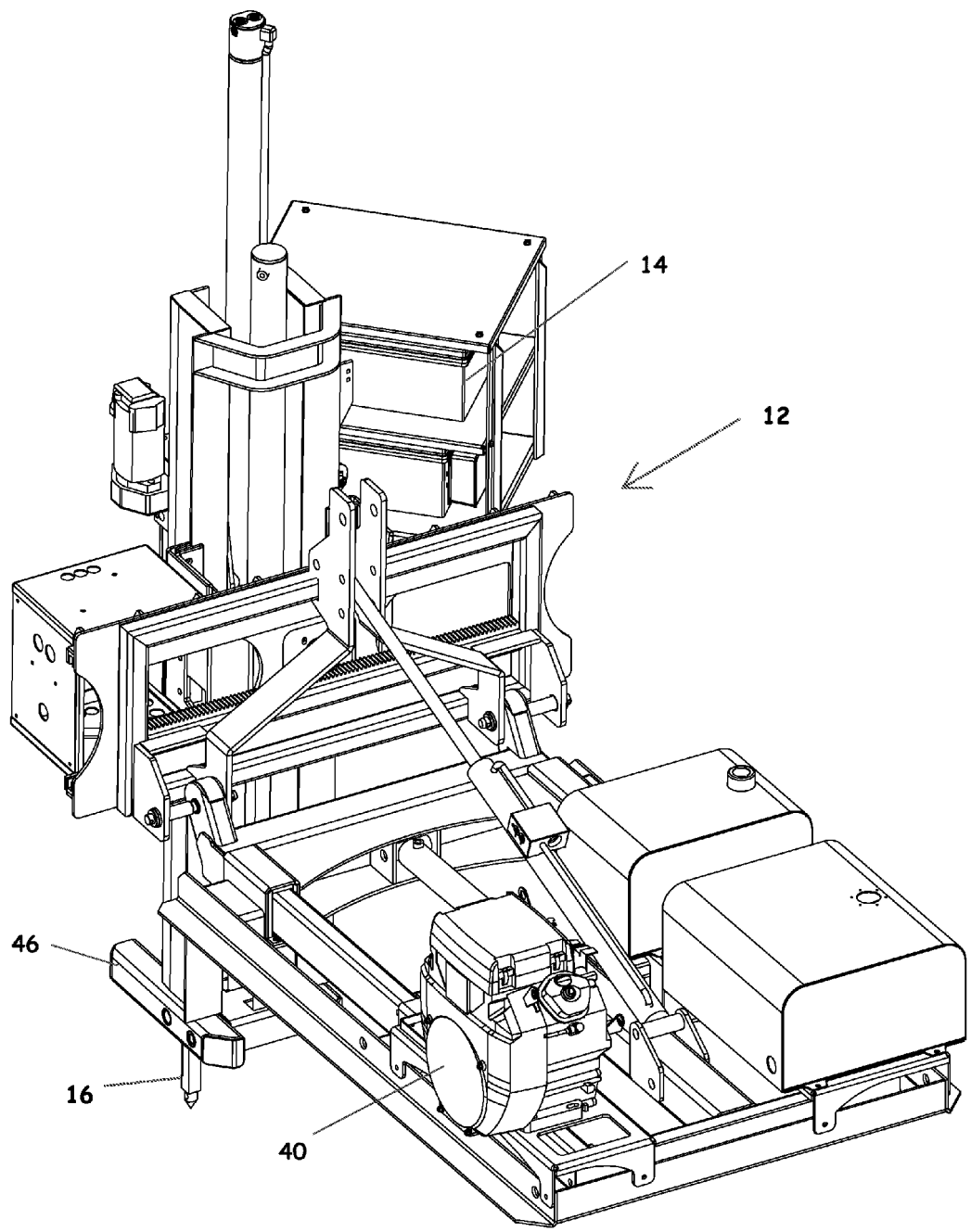
FIG. 5 is a perspective front view of the probe implement of FIG. 3.
Figure 6:
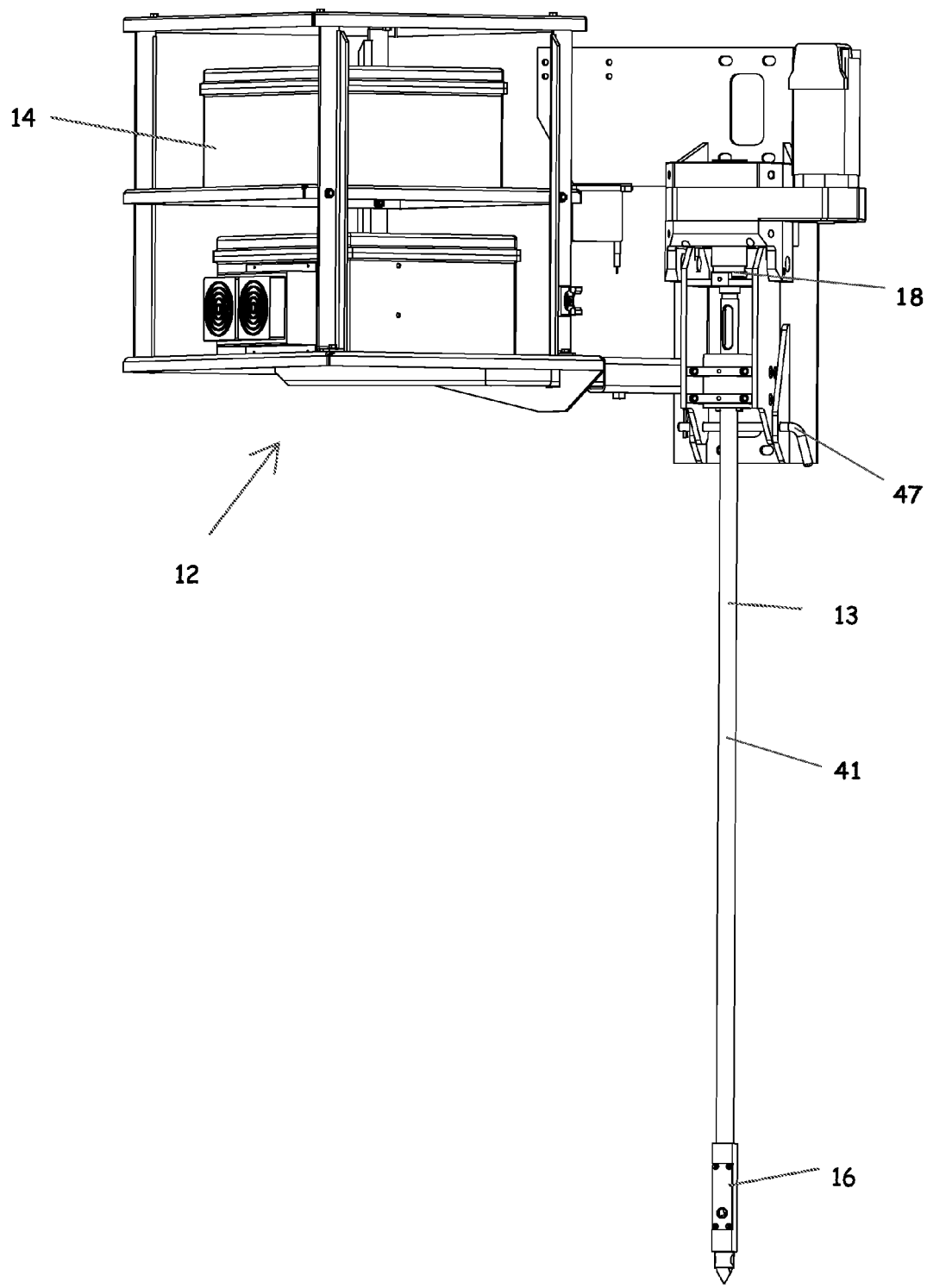
FIG. 6 is an elevation view of the probe implement of FIG. 3.
Figure 7:
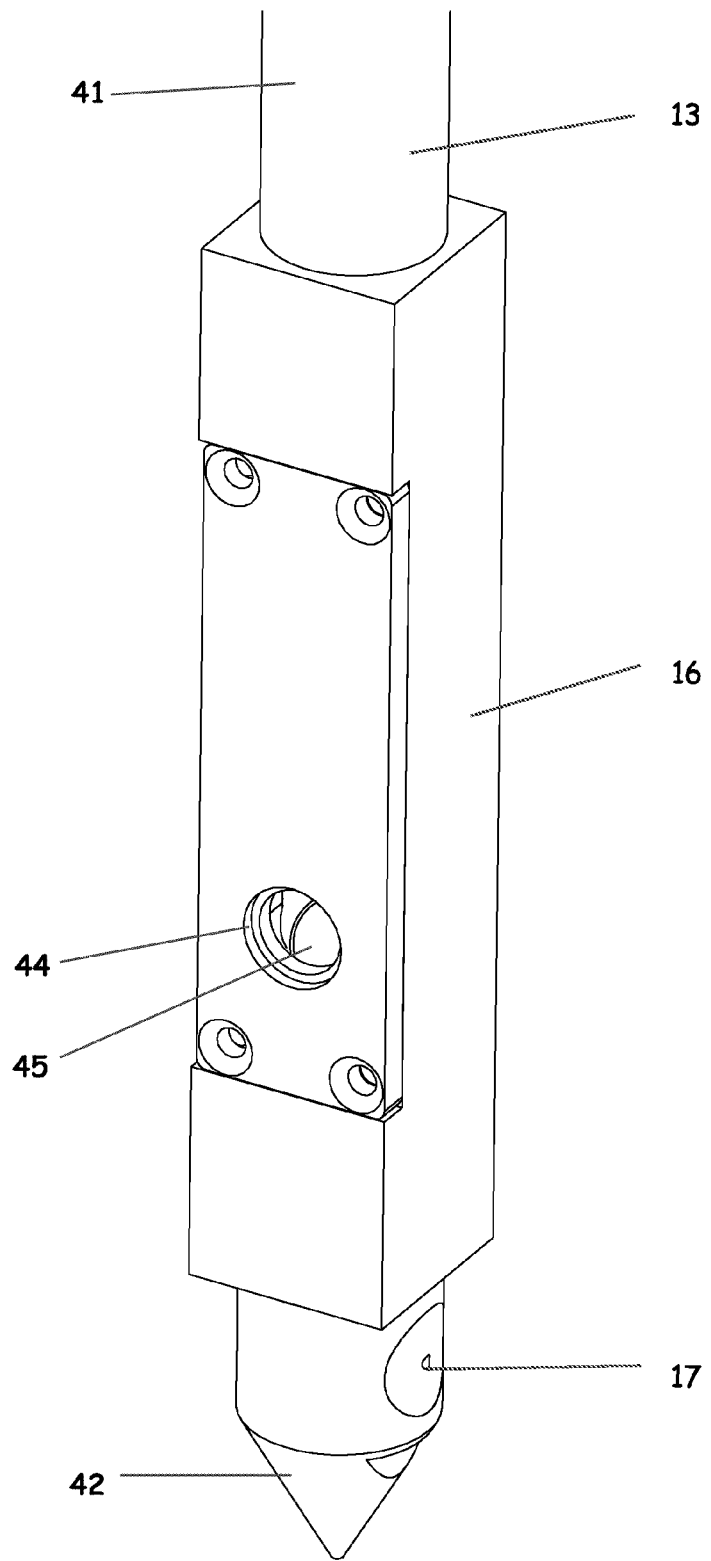
FIG. 7 is a perspective view of the reflectance module at the lower end of the sensor probe.
Figure 8:
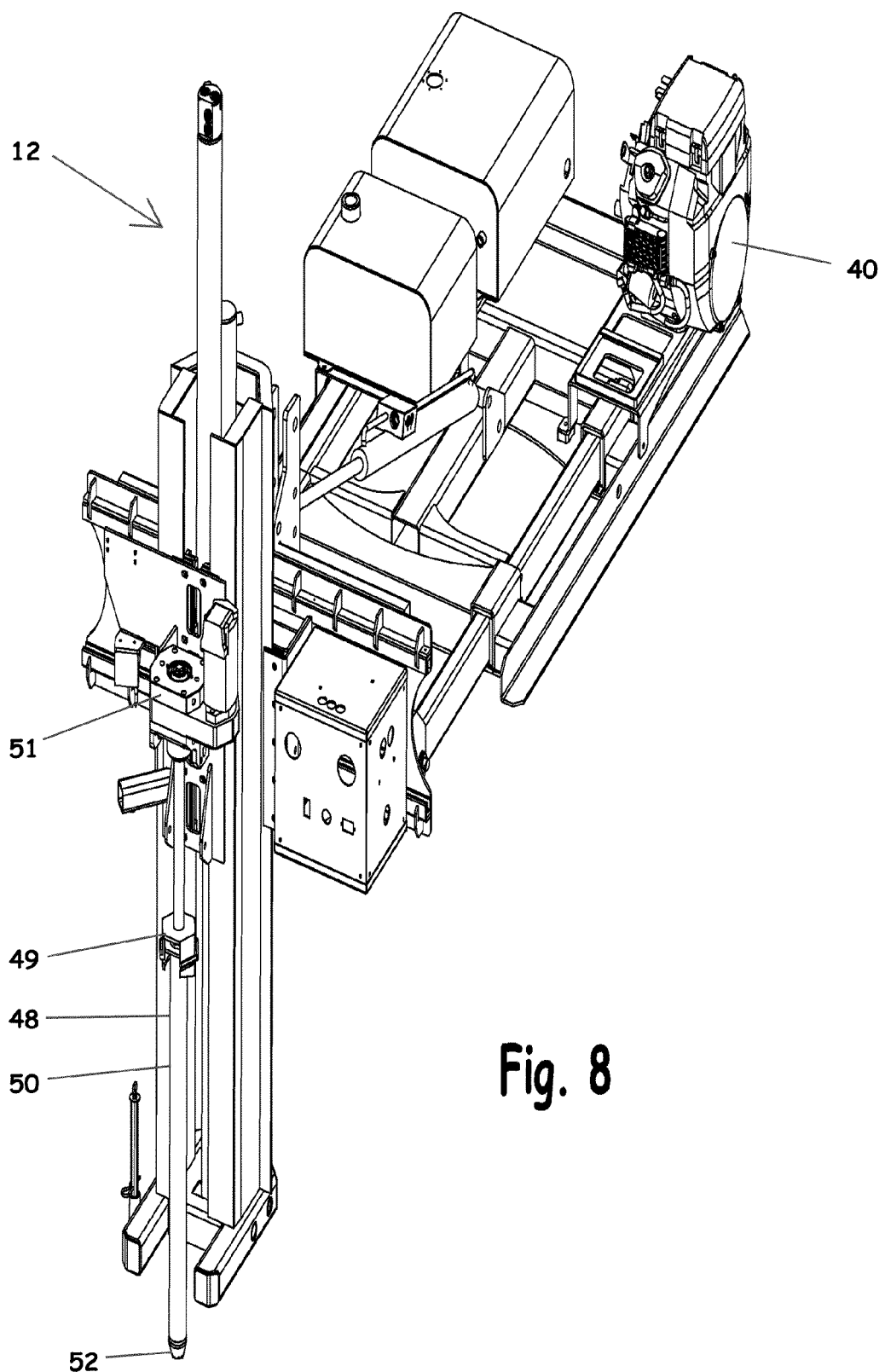
FIG. 8 is a rear perspective view of the probe implement with a coring probe attached for collecting soil cores.
Figure 9:
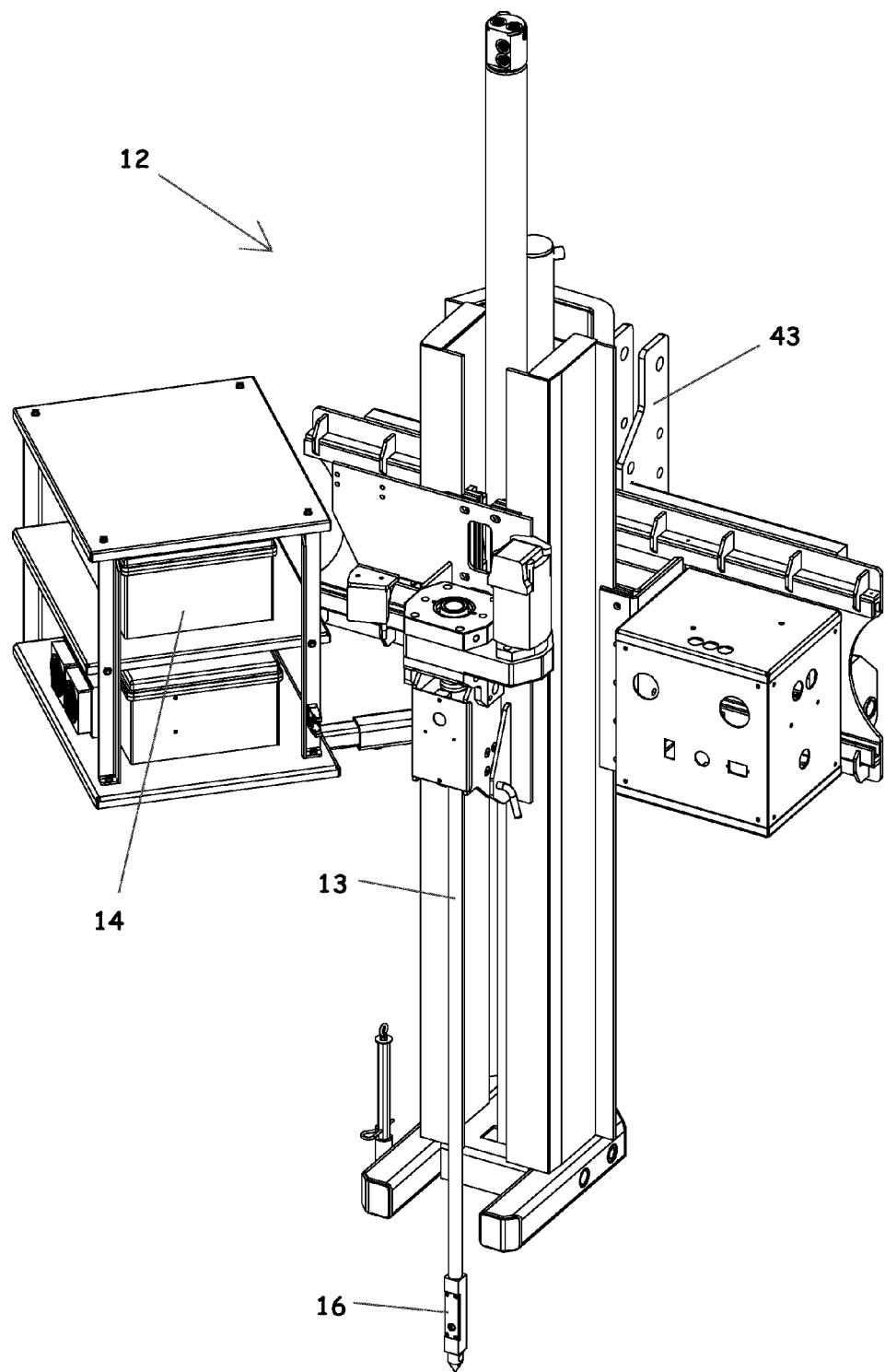
FIG. 9 is a rear perspective view of a probe implement according to another embodiment in which the probe implement is attached to a tractor via a 3-point hitch.
Figure 10:
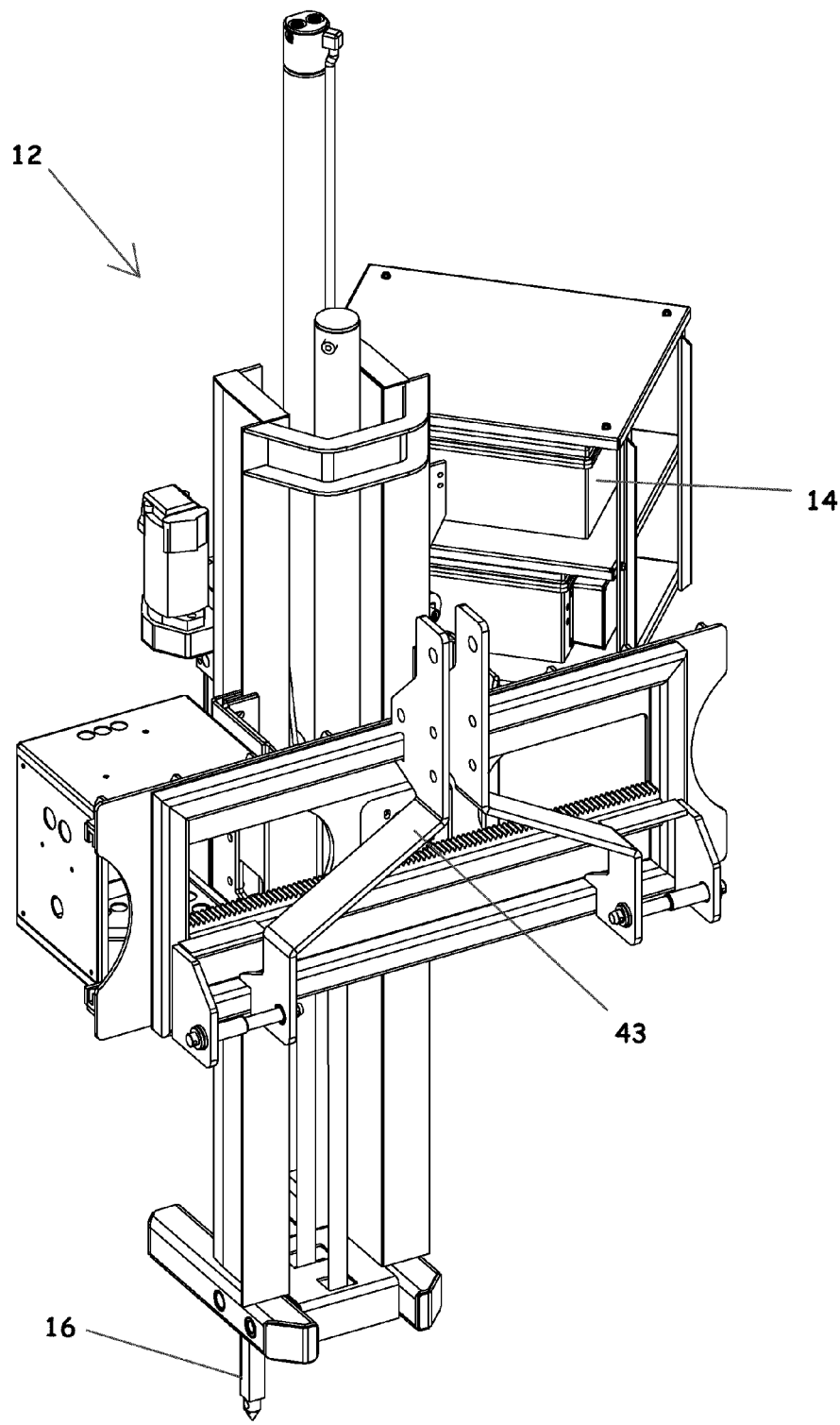
FIG. 10 is a front perspective view of the probe implement shown in FIG. 9.

The hydraulic functions of the probe implement 12 provide lateral and front-to-back shifting of the probe 13, as indicated by the arrows in FIG. 4. This allows repeated insertions in close proximity without moving the vehicle. The rack-and-pinion lateral shifting design keeps the entire probe implement 12 close-coupled to the vehicle. A hydraulic foot assembly 46 provides stability for the probe 13. The probe 13 is mounted to the implement with a single pin 47 for easy removal, allowing rapid installation of the coring probe 48, as described below.

The probe implement 12 also serves as the platform for hydraulically inserting a coring probe 48 into the soil. The coring probe 48 can be used to collect soil cores in close proximity to the sensor probe 13 insertions. The collected soil cores can then be lab-analyzed and used to calibrate the sensor measurements to soil properties of interest. The coring probe 48 is constructed of 2" OD steel, and attaches to the probe implement 12 with a coupler and hex-shaped locking collar 49. For ease of insertion, the core sampler tube 50 may be rotated with a hydraulic motor 51. The core sampler tube 50 has replaceable cutting shoes 52 that thread onto the tube 50. Samples may be collected in polymer liners that insert into the tube 50, or directly into the steel tube 50 itself.

Calibration to Soil Properties

In order to create a calibration to use the collected spectral data for quantitative predictions, a set of soil samples are needed that are representative of the spectral data space. The software processes the spectral data to determine optimal sample locations within the field, and within the soil profile. First, the spectra collected by the reflectance module of the shank implement are compressed using principal component analysis (PCA) and then grouped into 5 to 15 (user-selectable) clusters according to spectral properties. Subsequently, one location from each cluster is selected for soil sampling. The scores used for this compression are those corresponding to the eigenvectors of the covariance matrix having the largest eigenvalues. Clustering is performed using a fuzzy c-means algorithm. For each cluster, the sampling location is chosen so that it is close to the center of the cluster in spectral data space and geographically surrounded by the most points from the same cluster. At these sampling locations, the probe implement collects probe insertion data and adjacent soil core samples. The software processes the spectral data from the sensor probe to determine optimal portions of the soil cores to analyze, based on the same PCA, eigenvalue, and fuzzy c-means criteria used to determine where to probe. In summary, the software uses the sensor data collected from the X-Y axes to optimize where to probe the −Z axis, and the sensor data from the −Z axis to optimize sample analysis within the −Z axis profile. Once soil samples are analyzed, the results can be imported into third party chemometric software and calibrations created using techniques such as partial least-squares regression, and validated.

A flowchart showing the method steps for mapping soil properties in a field in three dimensions according to the present invention is shown in FIG. 11. According to this method, the first step 101 is to collect geo-referenced optical measurements of soil properties in an X-Y plane using the reflectance module 15 on the shank implement 10. This step 101 involves moving the shank implement 10 back and forth across the field in an array of transects with the reflectance module 15 collecting soil reflectance data from a predetermined shallow depth (e.g., 4 to 6 inches). The collected soil reflectance data from step 101 is then processed in step 102 to characterize the soil properties in the X-Y plane.

In step 103, the processed data is further processed to identify optimal sampling locations for conducting profile investigations using the probe implement 12. This further processing includes step 103*a* in which the spectral data from the shank implement is compressed using principal component analysis; step 103*b* in which the compressed spectral data is grouped into a plurality of clusters according to spectral properties; and step 103*c* in which one location is selected from each cluster for soil sampling using the probe implement 12. In step 104, optimal soil core collecting locations are identified from among the optimal sampling locations identified in step 103.

Once the optimal sampling locations are identified in step 103 and the optimal soil core collecting locations are identified in step 104, the probe implement 12 is moved to each of the sampling locations to conduct the profile investigations. In step 105, optical measurements of the soil properties are collected in a −Z axis direction (vertical) at each of the sampling locations using the reflectance module 16 on the probe implement 12.

In step 106, soil core samples are collected from the optimal soil core collecting locations, as determined in step 104. The soil core samples are analyzed in step 107 and used to calibrate the optical measurements collected by the probe implement 12.

A three-dimensional soil properties map is then created in step 108 based on the measurements collected from the shank implement 10 and the probe implement 12.

While the invention has been described in connection with specific embodiments thereof, it is to be understood that this is by way of illustration and not of limitation, and the scope of the appended claims should be construed as broadly as the prior art will permit.

What is claimed is:

1. A method of mapping soil properties in a field in three dimensions, comprising:

traversing a field with a reflectance module carried on a shank implement to collect optical measurements of soil properties in an X-Y plane at a first depth;

processing said collected optical measurements to characterize the variability of the soil properties in the X-Y plane;

identifying optimal sampling locations for profile investigations; and inserting a reflectance module carried on a probe implement vertically into the soil at said optimal sampling locations to collect optical measurements of soil properties in a −Z direction;

wherein identifying optimal sampling locations comprises:

compressing spectral data from the shank implement using principal component analysis;

grouping the compressed spectral data into a plurality of clusters according to spectral properties; and selecting one location from each cluster for soil sampling.

2. A method of mapping soil properties in a field in three dimensions, comprising:

traversing a field with a reflectance module carried on a shank implement to collect optical measurements of soil properties in an X-Y plane at a first depth;

processing said collected optical measurements to characterize the variability of the soil properties in the X-Y plane;

identifying optimal sampling locations for profile investigations; and inserting a reflectance module carried on a probe implement vertically into the soil at said optimal sampling locations to collect optical measurements of soil properties in a −Z direction;

wherein identifying optimal sampling locations comprises:

compressing spectral data from the shank implement using principal component analysis;

grouping the compressed spectral data into a plurality of clusters according to spectral properties; and selecting one location from each cluster for soil sampling; and wherein the step of compressing spectral data comprises using scores corresponding to the eigenvectors of a covariance matrix having the largest eigenvalues.

3. The method according to claim 2, wherein the step of grouping the compressed spectral data comprises using a fuzzy c-means algorithm to perform a clustering function.

4. The method according to claim 3, wherein the step of selecting one location from each cluster comprises selecting a sampling location close to a center of the cluster in spectral data space which is geographically surrounded by the most points from the same cluster.

5. A method of mapping soil properties in a field in three dimensions, comprising:

traversing a field with a reflectance module carried on a shank implement to collect optical measurements of soil properties in an X-Y plane at a first depth;

processing said collected optical measurements to characterize the variability of the soil properties in the X-Y plane;

using the collected optical measurements of soil properties in the X-Y plane to identify optimal sampling locations in the field for investigating a vertical soil profile; and inserting a reflectance module carried on a probe implement vertically into the soil profile in situ at said optimal sampling locations to collect additional optical measurements of soil properties in a −Z direction;

wherein said vertical soil profile extends below said first depth, and wherein said reflectance module carried on the probe implement is inserted vertically into the soil profile in the −Z direction below said first depth while maintaining the probe implement stationary in an X-Y direction at said optimal sampling locations.

6. The method according to claim 5, further comprising identifying optimal soil core collecting locations from among said optimal sampling locations, and collecting soil core samples from said soil core collecting locations.

7. The method according to claim 6, further comprising lab-analyzing the soil core samples to calibrate the optical measurements collected by the probe implement.

8. The method according to claim 5, wherein identifying optimal sampling locations comprises processing spectral data from said collected optical measurements of soil properties in the X-Y plane to determine optimal sample locations within the field and within the soil profile.

* * * * *